United States Patent [19]

Razi

[11] 4,411,653
[45] Oct. 25, 1983

[54] CANNULA INTRODUCER

[76] Inventor: M. Dean Razi, 5800-49th St. N., St. Petersburg, Fla. 33709

[21] Appl. No.: 343,408

[22] Filed: Jan. 28, 1982

[51] Int. Cl.³ ............................................. A61M 5/00
[52] U.S. Cl. .................................. 604/157; 604/164; 128/305
[58] Field of Search ................. 604/165, 164, 166, 51, 604/117, 224, 156, 157; 128/305

[56] References Cited

U.S. PATENT DOCUMENTS

| | | | |
|---|---|---|---|
| 3,051,172 | 8/1962 | Bruchhaus | 604/224 |
| 3,538,916 | 11/1970 | Wiles et al. | 604/117 X |
| 3,762,416 | 10/1973 | Moss et al. | 128/305 |
| 4,292,970 | 10/1981 | Hession, Jr. | 604/157 |

*Primary Examiner*—Stephen C. Pellegrino
*Attorney, Agent, or Firm*—Ronald E. Smith

[57] ABSTRACT

Surgical devices of the type designed to facilitate insertion of aortic cannula. A first embodiment includes a long, spring-loaded blade-carrying stylet, a housing designed to receive the stylet and a cannula that is carried and guided by the housing. The surgeon positions the distal end of the device at the point of the aorta where the cannula is to be inserted, momentarily depresses the proximal end of the stylet to make the desired cut, and advances the cannula into position using the stylet housing as a guide means. A semi-automatic embodiment advances the cannula responsive to the pulling of a trigger but retains the manual manipulation of the blade-carrying stylet. An automatic embodiment includes the trigger mechanism for inserting the cannula, and further includes a second trigger for advancing and retracting the blade-carrying stylet.

5 Claims, 6 Drawing Figures

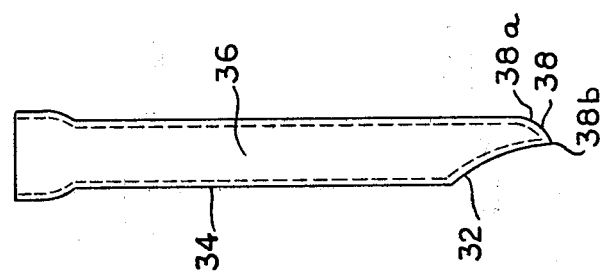
FIG_3
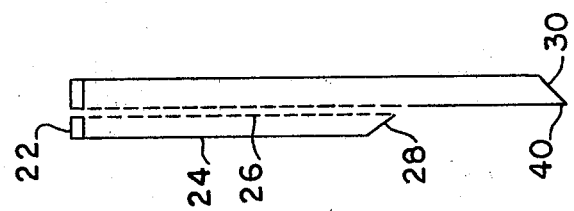
FIG_2
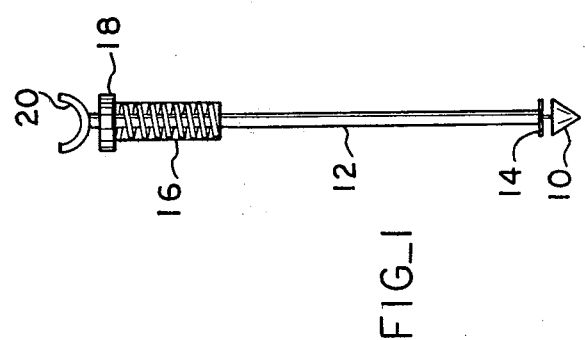
FIG_1

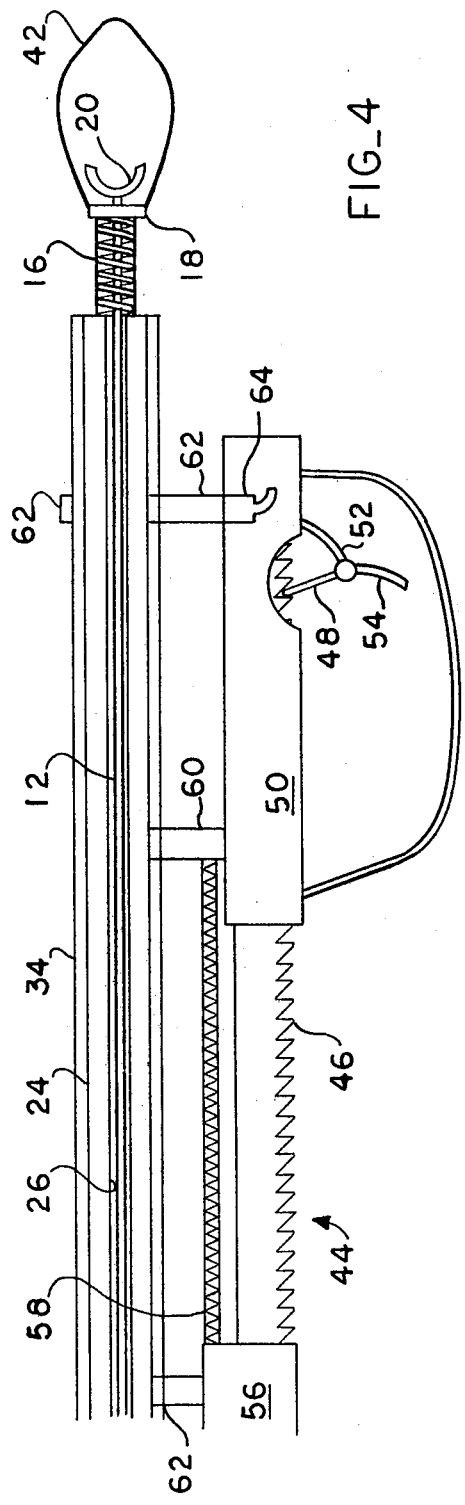
FIG_4
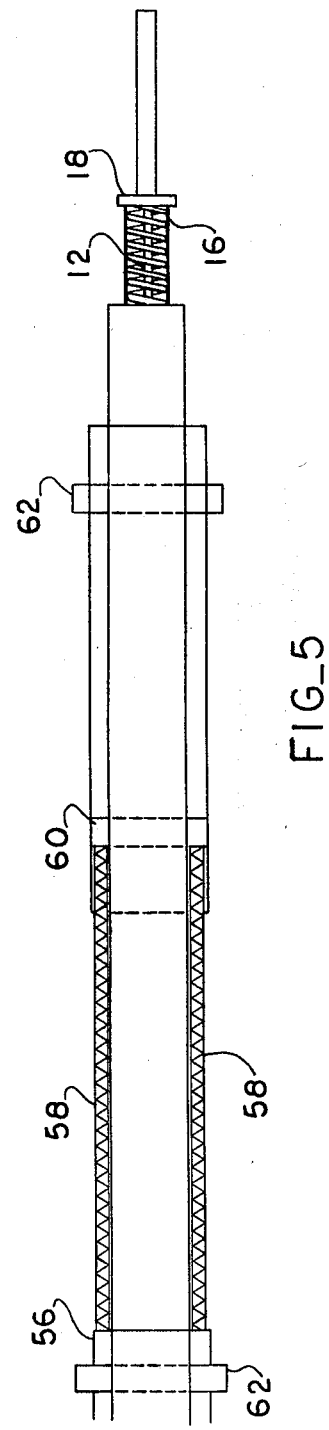
FIG_5

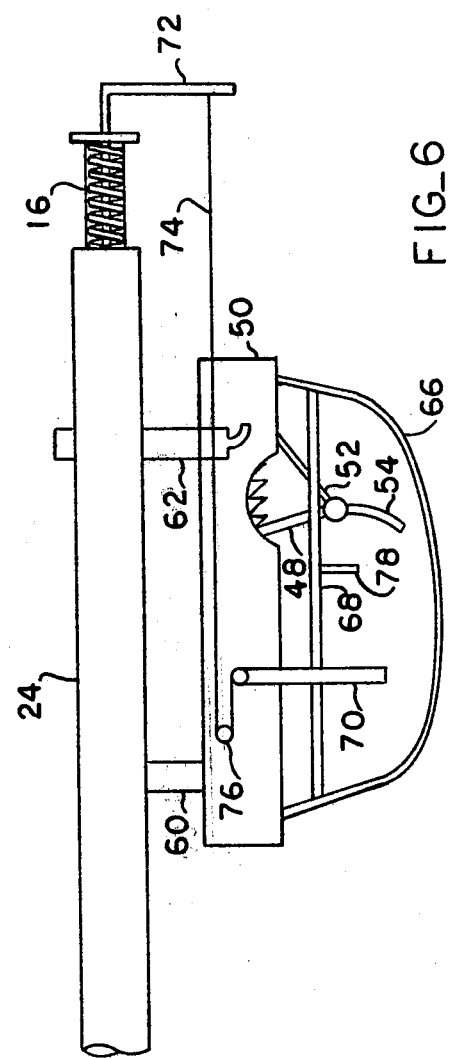

CANNULA INTRODUCER

BACKGROUND OF THE INVENTION

1. Field of the Invention

This invention relates, generally, to surgical devices, and more particularly relates to devices having utility in the field of heart operations of any type where the operation requires that the functions of the heart be performed by a machine to which the patient is connected during surgery.

2. Description of the Prior Art

A search of United States patents located the following patents:

| Patentee | U.S. Pat. No. | Date of Issue |
| --- | --- | --- |
| Hill et. al. | 3,776,237 | 12-04-73 |
| Goosen | 4,018,228 | 04-19-77 |
| Peyman | 4,099,529 | 07-11-78 |
| Downie et. al. | 4,216,776 | 08-12-80 |
| Lary | 4,273,128 | 06-16-81 |

The field of search covered Class/Subclass 128/246,305,305.2, and 305.3.

The surgical instruments that are disclosed in the above-listed patents are used to form perforations in the aorta to facilitate subsequent introduction of a cannula, after a slit has been made in the aorta in the conventional manner-with a scalpel. Such devices thus have little relevance in the field of this invention.

No surgical instruments are known that eliminate the use of the scalpel when making a slit in the aorta to allow insertion of a cannula into such aorta. Nor are any instruments known that guide the actual insertion of the cannula after the slit has been made.

A properly designed instrument would lower the level of skill required to perform the cannula insertion, thereby reducing the risk of the procedure. Such an instrument would produce slits that would be precisely the width required for the insertion. Slits of greater width than that required allow bleeding around the perimeter of the inserted tube, and slits of smaller width than required often result in tears in the aorta as the cannula is forced through a too small opening.

There is clearly a need for a surgical instrument that is easy to use, that produces an optimal-size slit in the aorta and that introduces the cannula in a uniform manner, but the required instrument is not found in the prior art.

SUMMARY OF THE INVENTION

The longstanding but heretofore unfulfilled need for a cannula introducer is now fulfilled in the form of a surgical instrument that has three (3) closely related embodiments.

The first embodiment provides a rod-like housing that has three functions—it provides a guide means for the cannula as the cannula is axially advanced through the slit, it provides a guide means for a blade-carrying stylet that is slideably mounted in an axial bore formed in such housing, and it protects the cannula from cutting by the blade when the blade is extended from and retracted into said housing.

The second embodiment features a cradle means that carries the cannula and the housing slideably disposed therein. The cannula is secured to an axially moveable base member that is spring loaded and trigger activated so that the cannula is introduced through the slit responsive to activation of said trigger, thereby assuring uniformity in the introduction procedure.

The third embodiment includes a cable member that is operably connected to a second trigger so that squeezing said second trigger advances the blade in an axial direction, thereby effecting the desired cut. As in the first two (2) embodiments of the invention, the blade is spring loaded so that release of the second trigger allows retraction of the blade after the cut has been made. Pulling the first-mentioned trigger then effects the introduction of the cannula.

It is therefore seen that a primary object of this invention is to provide a surgical tool that makes uniform-size slits in the aorta.

A closely related object of the invention is to provide such a tool that effects introduction of a cannula having an outside diameter substantially equal to the diameter of a slit formed by the tool.

A more general object is to provide a device that is economically feasible, easy to use and safe.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a front perspective view of the novel blade-carrying stylet.

FIG. 2 is a side perspective view of the novel housing.

FIG. 3 is a side perspective view of a cannula, having its distal end specifically cut in accordance with the teachings of this invention.

FIG. 4 is a side elevational view of the second embodiment, showing the cannula and housing in vertical section and showing the balance of the instrument in perspective.

FIG. 5 is a top plan perspective view of the embodiment shown in FIG. 4.

FIG. 6 is a side elevational view showing the third embodiment of the invention.

DETAILED DESCRIPTION OF THE PREFERRED EMBODIMENTS

Referring now to FIG. 1, it will there be seen that the blade 10 that forms the desired slit in the aorta to make a passageway that allows introduction of the cannula into the aorta is preferably arrowhead-shaped. The blade 10 is integrally formed with or fixedly secured to the distal end of an elongate rod or stylet 12. A transversely disposed guard member 14 is formed just rearwardly, or proximally, of the blade 10, and permits the blade to be withdrawn from the aorta in a safe manner.

A bias means such as a spring 16 surrounds the proximal end of the stylet 12 when the instrument is in use. The proximal end of the spring 16 abuts the underside, or distal surface of the base portion 18 of the thumb rest 20 which the surgeon depresses to effect travel of the blade 10 in an axial, proximal-to-distal direction when it is desired to slit the aorta. The distal end of the spring 16 abuts the proximal end 22 of the housing 24, shown in FIG. 2, when the device is assembled.

As shown in FIG. 2, the housing 24 is a rod-like member having an axial bore 26 formed therein. The distal end of the housing 24 is beveled as at 28 and as at 30, bevel cut 30 being formed in a manner complemental to the bevel 38 formed in the distal end of the cannula 34 that is shown in FIG. 3. The cannula 34 is rounded as at 38a, and the opposite side 32 thereof is gently curved, in bird beak fashion as shown.

When the first embodiment of the invention is in its assembled configuration, the stylet 12 is slideably disposed within bore 26 of housing 24 so that the spring 16 is disposed in sandwiched relation between shoulder 22 (FIG. 2) and the base 18 (FIG. 1). The length of the bore 26 serves to stabilize the blade 10 against wobbling. The stylet 12 and housing 24, in their above-described assembled configuration, are disposed within the hollow interior 36 of the tubular cannula 34. When the housing 24 is properly positioned within the cannula 34, beveled edge 30 of the housing 24 will be aligned with beveled edge 38 of the cannula 34. The flat blade 10 will be disposed exterior to the bore 26, but will not abrade the cannula 34 because the cross sectional diameter of the housing 24 is greater than the width of the blade 10.

To use the embodiment of FIGS. 1–3, the surgeon positions the distal tip 38b of the cannula 34 and hence the distal tip 40 of the housing 24 at the point on the aorta that has been preselected for insertion of the cannula 34. He or she then depresses thumb rest 20 so that blade 10 extends axially beyond tips 38b and 40 and thus enters into cutting relation with the preselected point on the aorta (not shown). The rest 20 is depressed until the desired slit has been completed, and the pressure against the rest 20 is then decreased to allow retraction of the blade 10 attendant unloading of spring 16. The surgeon retains the housing 24 and the cannula 34 in a substantially still position during this procedure. After blade 10 has retracted into its original position, the surgeon slides the cannula 34 through the slit and into the aorta a preselected distance, using the stationary housing 34 as a guide means during such introduction procedure. The width of the slit will be only slightly less than the diameter of the cannula 34, and the elasticity of the aorta will allow insertion of the cannula in the absence of any tearing action. The resulting fit of the aorta about the cannula 34 will be such that no blood will leak around the perimeter of the cannula 34, which leakage is commonly encountered when the slit is made in the conventional fashion.

Having inserted the cannula 34, the surgeon slowly retracts the housing 24 therefrom. Blood will enter the cannula 34 as the housing 24 axially retreats therefrom. After the housing 24 has been retracted a preselected distance in accordance with good surgical practice, a clamp-not shown-is placed on the cannula to block further blood travel up the cannula 34 and the housing 24 is completely withdrawn from the cannula 34 after the clamp is in place. The proximal end of the cannula 34 is then brought into fluid communication with a machine that performs the functions of the heart and lungs and the clamp is removed so that blood processed by said machine can flow from the machine, through the cannula 34, and into the aorta for subsequent distribution throughout the body so that the now-disabled heart can be surgically treated.

FIGS. 4 and 5 show a second embodiment of the invention, which embodiment is characterized by a cannula inserting mechanism that frees the surgeon from physically advancing the cannula into the slit. The cannula 34, housing 24 and stylet 12 are the same as in the first-described embodiment, although ring 42 is added to help maintain the surgeon's thumb on the thumb rest 20 when it is depressed as disclosed in connection with the first embodiment to make the required slit.

The added elements include a rack gear 44 having a plurality of axially aligned, equidistantly spaced, unidirectionally oriented teeth 46, and a spring-loaded pawl member 48 that engages said teeth 46 in the conventional manner. A slideably mounted base member 50 is connected to pawl 48 by link 52, and a first trigger means 54 is operative to engage and disengage said pawl 48 and teeth 46 attendant release and pulling of said trigger 54, respectively. When the trigger 54 is pulled, thereby disengaging pawl 48 from teeth 46, as aforesaid, base 50 is free to move axially in either direction as guided by rack gear member 44.

An anchor member 56 is integrally formed with the rack 44 at its distal end, and provides a mounting means for a pair of longitudinally aligned, transversely spaced bias members 58, the other end of said springs 58 being anchored to a second mounting means 60 that is fixedly secured to and conjointly movable with the base member 50. Accordingly, a distal-to-proximal motion of the base 50, i.e., a left to right movement as depicted in FIGS. 4 and 5, will load springs 58, but the pawl 48 will prevent a reverse direction, spring unloading motion. Such motion will result, clearly, when trigger 54 is activated to release the pawl 48 from engagement with teeth 46.

The cannula 34, and the stylet-carrying housing 24 disposed therein, are mounted atop the base member 50 and the mounting member 56 by a pair of longitudinally spaced cradle means 62. A hook member 64 unites the proximal cradle 62 and the base 50 so that axial movement of the base 50 is translated to the cannula/housing assembly. Accordingly, the physician loads the springs 58 by retracting the base 50, positions the assembly so that the slit will be properly formed, depresses thumb rest 20 to make the slit, and pulls trigger 54 to introduce the cannula 34 into the aorta. The mounting means 56 stops the forward travel of the cannula 34, it being understood that the physician determines the depth of cannula insertion by the distance the base 50 is retracted relative to such stopping means 56. To aid the surgeon, a mark-not-shown-is made on the cannula when it is manufactured so that the amount of base member "cocking" is readily indicated.

It is also to be noted that a trigger guard 66 is provided for safety purposes, and that mounting member 60 also serves to support the cannula 34, thus complementing the cannula-support function of cradle members 62.

The trigger guard 66 is modified for the third embodiment to have a bar 68 that provides a rail upon which a second trigger means 70 is slideably mounted for axial travel. In this embodiment, stylet 12 is bent as at 72 and a substantially non-extensible cable member 74 is employed to interconnect the bent portion 72 of the stylet 12 and the trigger 70, said cable 70 defining a path of travel as shown in FIG. 3, having a reverse bend about roller 76. Pulling trigger 70 thus advances the stylet 12 so that blade 10 makes the desired cut. This loads spring 16 so that releasing trigger 70 allows spring 16 to resume its equilibrium position, thereby retracting the blade 10. The first-mentioned trigger 54 is then pulled to effect introduction of the cannula 34 in the manner heretofore described.

A stop member 78 depends to bar 68 and serves to limit the depth of blade 10 penetration by limiting the distance the trigger 70 can be pulled.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, that which is claimed is:

1. A surgical device for insertion of aortic cannula of the type including an elongate, thin rod member, a blade member integrally formed with said rod member, disposed at the distal end of said rod member, an elongate housing member, an elongate bore formed in said housing member, substantially centrally thereof, wherein said rod member is slideably disposed interiorly of said bore and movably mounted therein between a blade member-extended position and a blade member-retracted position, a bias means disposed at the proximal end of said rod member for retaining said blade member in its retracted position in the absence of external, longitudinally directed forces imparted against said rod member, and an elongate, flexible cannula member having said housing member slideably disposed therein, wherein the improvement comprises:

a trigger-operated means for effecting the longitudinal displacement of said cannula member into an aorta through a cut made by said blade member,
   said trigger-operated means comprising a hollow, longitudinally disposed base member,
   an elongate rack gear member slideably disposed interiorly of said blade member,
   a pawl member operatively disposed relative to said gear member and operable to allow unidirectional movement of said base member when said pawl member engages said gear member,
   a trigger member operatively secured to said pawl member,
   a longitudinally disposed second bias means having a stationary distal end and a proximal end fixedly secured to said base member so that sliding said base member in a distal-to-proximal direction loads said second bias means,
   a clamping member for securing said cannula member to said base member,
   a hook member associated with said clamping member,
   said trigger member operatively connected to said hook member,
   whereby said cannula member is prepared for aortic insertion by manually retracting said base member, thereby retracting said cannula member, said retraction loading said second bias means, and said pawl member, co-acting with said gear member, operable to prevent untimely unloading of said second bias means, and whereby manual activation of said trigger member is operative to disengage said pawl member from said gear member and is further operative to disengage said hook member from said bias member to the end that such trigger activation allows said second bias means to unload, thereby driving said cannula member in a proximal-to-distal direction so that said cannula is thrust through the cut made in said aorta prior to activation of said trigger member.

2. The surgical device of claim 1, further comprising a second trigger-activated means for advancing said blade member in a proximal-to-distal direction so that a cut is made in said aorta by said blade member responsive to manual activation of said second trigger activated means, said second trigger activated means comprising, a projecting member integrally formed with said elongate rod member, at the distal end of said rod member,
   a slideably mounted second trigger member,
   an elongate, substantially non-extensible cable member disposed in connecting relation between said second trigger member and said projecting portion of said rod member,
   a roller member disposed distally remote from said second trigger member,
   and said cable member defining a path of travel from said projecting portion, around said roller member and to said second trigger member,
   whereby distal-to-proximal travel of said second trigger member substantially simultaneously effects a proximal-to-distal travel of said blade member-carrying rod member, said former direction of travel operative to load said first bias means, and said latter direction of travel operative to unload said first bias means.

3. The surgical device of claim 2, wherein said housing member has a diagonal cut formed at its distal end, and wherein said cannula member has a complementally formed cut at its distal end so that insertion of said cannula member through said cut is facilitated and so that said housing member protects said cannula member from abrading by said blade member.

4. The surgical device of claim 2, wherein said blade member has a leading portion having an arrow head configuration, and a trailing portion formed of a transversely disposed, blunted guard member that protects the aorta during retraction of said blade member from said aorta.

5. The surgical device of claim 3, wherein a pair of longitudinally spaced cradling members are fixedly secured to said base member so that said cannula member are releasably cradled therein.

* * * * *